US008204296B2

(12) United States Patent
Bhaskar et al.

(10) Patent No.: US 8,204,296 B2
(45) Date of Patent: Jun. 19, 2012

(54) METHODS FOR GENERATING A STANDARD REFERENCE DIE FOR USE IN A DIE TO STANDARD REFERENCE DIE INSPECTION AND METHODS FOR INSPECTING A WAFER

(75) Inventors: Kris Bhaskar, San Jose, CA (US); Mark McCord, Mountain View, CA (US); Santosh Bhattacharyya, San Jose, CA (US); Ardis Liang, Fremont, CA (US); Richard Wallingford, San Jose, CA (US); Hubert Altendorfer, Redwood Shores, CA (US); Kais Maayah, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 50 days.

(21) Appl. No.: 12/881,669

(22) Filed: Sep. 14, 2010

(65) Prior Publication Data
US 2010/0329540 A1    Dec. 30, 2010

Related U.S. Application Data

(62) Division of application No. 12/176,095, filed on Jul. 18, 2008, now Pat. No. 7,796,804.

(60) Provisional application No. 60/950,974, filed on Jul. 20, 2007.

(51) Int. Cl.
*G06K 9/00* (2006.01)
(52) U.S. Cl. .................... 382/145; 382/103; 382/149
(58) Field of Classification Search ............ 382/103, 382/115, 145
See application file for complete search history.

(56) References Cited

U.S. PATENT DOCUMENTS

| | | | |
|---|---|---|---|
| 3,495,269 | A | 2/1970 | Mutschler et al. |
| 3,496,352 | A | 2/1970 | Jugle |
| 3,909,602 | A | 9/1975 | Micka |
| 4,015,203 | A | 3/1977 | Verkuil |
| 4,247,203 | A | 1/1981 | Levy et al. |
| 4,347,001 | A | 8/1982 | Levy et al. |
| 4,378,159 | A | 3/1983 | Galbraith |
| 4,448,532 | A | 5/1984 | Joseph et al. |
| 4,532,650 | A | 7/1985 | Wihl et al. |
| 4,555,798 | A | 11/1985 | Broadbent, Jr. et al. |

(Continued)

FOREIGN PATENT DOCUMENTS
EP        0032197        7/1981
(Continued)

OTHER PUBLICATIONS

U.S. Appl. No. 60/681,095, filed May 13, 2005 by Nehmadi et al.
(Continued)

*Primary Examiner* — Stephen R Koziol
(74) *Attorney, Agent, or Firm* — Ann Marie Mewherter

(57) ABSTRACT

Methods for generating a standard reference die for use in a die to standard reference die inspection and methods for inspecting a wafer are provided. One computer-implemented method for generating a standard reference die for use in a die to standard reference die inspection includes acquiring output of an inspection system for a centrally located die on a wafer and one or more dies located on the wafer. The method also includes combining the output for the centrally located die and the one or more dies based on within die positions of the output. In addition, the method includes generating the standard reference die based on results of the combining step.

16 Claims, 5 Drawing Sheets

U.S. PATENT DOCUMENTS

| | | |
|---|---|---|
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano, Jr. et al. |
| 4,633,504 A | 12/1986 | Wihl |
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,189,481 A | 2/1993 | Jann et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 6,011,404 A | 1/2000 | Ma et al. |
| 6,014,461 A | 1/2000 | Hennessey et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,224,638 B1 | 5/2001 | Jevtic et al. |
| 6,233,719 B1 | 5/2001 | Hardikar et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,373,975 B1 | 4/2002 | Bula et al. |
| 6,415,421 B2 | 7/2002 | Anderson et al. |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |

| Patent No. | Date | Inventor |
|---|---|---|
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,379,175 B1 | 5/2008 | Stokowski et al. |
| 7,386,839 B1 | 6/2008 | Golender et al. |
| 7,418,124 B2 | 8/2008 | Peterson et al. |
| 7,424,145 B2 | 9/2008 | Horie et al. |
| 7,683,319 B2 | 3/2010 | Makino et al. |
| 7,738,093 B2 | 6/2010 | Alles et al. |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0014146 A1 | 1/2003 | Fujii et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1* | 3/2003 | Lehman .................. 382/144 |
| 2003/0057971 A1 | 3/2003 | Nishiyama et al. |
| 2003/0086081 A1 | 5/2003 | Lehman |
| 2003/0098805 A1 | 5/2003 | Bizjak et al. |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0052411 A1 | 3/2004 | Qian et al. |
| 2004/0057611 A1 | 3/2004 | Lee et al. |
| 2004/0091142 A1 | 5/2004 | Peterson et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0174506 A1 | 9/2004 | Smith |
| 2004/0223639 A1 | 11/2004 | Sato et al. |
| 2004/0228515 A1 | 11/2004 | Okabe et al. |
| 2004/0243320 A1 | 12/2004 | Chang et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0062962 A1 | 3/2005 | Fairley et al. |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner et al. |
| 2006/0000964 A1 | 1/2006 | Ye et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1* | 8/2006 | Dorphan et al. .............. 382/145 |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0013901 A1 | 1/2007 | Kim et al. |
| 2007/0019171 A1 | 1/2007 | Smith |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1* | 2/2007 | Kekare et al. .............. 356/237.5 |
| 2007/0052963 A1 | 3/2007 | Orbon et al. |
| 2007/0064995 A1 | 3/2007 | Oaki et al. |
| 2007/0133860 A1 | 6/2007 | Lin et al. |

| | | | |
|---|---|---|---|
| 2007/0156379 | A1 | 7/2007 | Kulkarni et al. |
| 2007/0230770 | A1 | 10/2007 | Kulkarni et al. |
| 2007/0248257 | A1 | 10/2007 | Bruce et al. |
| 2007/0280527 | A1 | 12/2007 | Almogy et al. |
| 2007/0288219 | A1 | 12/2007 | Zafar et al. |
| 2008/0013083 | A1 | 1/2008 | Kirk et al. |
| 2008/0049994 | A1 | 2/2008 | Rognin et al. |
| 2008/0163140 | A1 | 7/2008 | Fouquet et al. |
| 2008/0167829 | A1 | 7/2008 | Park et al. |
| 2008/0250384 | A1 | 10/2008 | Duffy et al. |
| 2008/0304056 | A1 | 12/2008 | Alles et al. |
| 2009/0024967 | A1 | 1/2009 | Su et al. |
| 2009/0037134 | A1 | 2/2009 | Kulkarni et al. |
| 2009/0041332 | A1 | 2/2009 | Bhaskar et al. |
| 2009/0043527 | A1 | 2/2009 | Park et al. |
| 2009/0055783 | A1 | 2/2009 | Florence et al. |
| 2009/0080759 | A1 | 3/2009 | Bhaskar et al. |
| 2009/0257645 | A1 | 10/2009 | Chen et al. |

FOREIGN PATENT DOCUMENTS

| | | |
|---|---|---|
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1480034 | 11/2004 |
| EP | 1696270 | 8/2006 |
| JP | 2002071575 | 3/2002 |
| JP | 2003-215060 | 7/2003 |
| JP | 2005-283326 | 10/2005 |
| KR | 10-2001-0037026 | 5/2001 |
| KR | 10-2001-0101697 | 11/2001 |
| KR | 1020030055848 | 7/2003 |
| KR | 10-2006-0075691 | 7/2006 |
| WO | 9957358 | 12/1998 |
| WO | 9922310 | 5/1999 |
| WO | 9925004 | 5/1999 |
| WO | 9959200 | 5/1999 |
| WO | 9938002 | 7/1999 |
| WO | 9941434 | 8/1999 |
| WO | 0003234 | 1/2000 |
| WO | 0036525 | 6/2000 |
| WO | 0055799 | 9/2000 |
| WO | 0068884 | 11/2000 |
| WO | 0070332 | 11/2000 |
| WO | 0109566 | 2/2001 |
| WO | 0140145 | 6/2001 |
| WO | 03104921 | 12/2003 |
| WO | 2004027684 | 4/2004 |
| WO | 2006063268 | 6/2006 |
| WO | 2010/093733 | 8/2010 |

OTHER PUBLICATIONS

U.S. Appl. No. 60/684,360, filed May 24, 2005 by Nehmadi et al.
U.S. Appl. No. 10/778,752, filed Feb. 13, 2004 by Preil et al.
U.S. Appl. No. 10/793,599, filed Mar. 4, 2004 by Howard et al.
U.S. Appl. No. 11/139,151, filed Feb. 10, 2005 by Volk.
U.S. Appl. No. 11/154,310, filed Feb. 10, 2005 by Verma et al.
U.S. Appl. No. 12/394,752, filed Feb. 27, 2009 by Xiong et al.
U.S. Appl. No. 12/403,905, filed Mar. 13, 2009 by Xiong.
Allan et al., "Critical Area Extraction for Soft Fault Estimation," IEEE Transactions on Semiconductor Manufacturing, vol. 11, No. 1, Feb. 1998.
Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automated Defect Severity Scoring," Proceedings of the SPIE, vol. 4409, Jan. 2001, pp. 467-478.
Comizzoli, "Uses of Corona Discharges in the Semiconductor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and production metrology of thin transistor gate oxide films," Materials Science in Semiconductor Processing 2, 1999, pp. 103-147.
Dirksen et al., "Impact of high order aberrations on the performance of the aberration monitor," Proc. of SPIE vol. 4000, Mar. 2000, pp. 9-17.
Dirksen et al., "Novel aberration monitor for optical lithography," Proc. of SPIE vol. 3679, Jul. 1999, pp. 77-86.
Garcia et al., "New Die to Database Inspection Algorithm for Inspection of 90-nm Node Reticles," Proceedings of SPIE, vol. 5130, 2003, pp. 364-374.
Granik et al- "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
International Search Report for PCT/US2003/021907 mailed Jun. 7, 2004.
International Search Report for PCT/US2004/040733 mailed Dec. 23, 2005.
International Search Report for PCT/US2006/061112 mailed Sep. 25, 2008.
International Search Report for PCT/US2006/061113 mailed Jul. 16, 2008.
International Search Report for PCT/US2008/050397 mailed Jul. 11, 2008.
International Search Report for PCT/US2008/062873 mailed Aug. 12, 2008.
International Search Report for PCT/US2008/062875 mailed Sep. 10, 2008.
International Search Report for PCT/US2008/063008 mailed Aug. 18, 2008.
International Search Report for PCT/US2008/066328 mailed Oct. 1, 2009.
International Search Report for PCT/US2008/070647 mailed Dec. 16, 2008.
International Search Report for PCT/US2008/072636 mailed Jan. 29, 2009.
International Search Report for PCT/US2008/073706 mailed Jan. 29, 2009.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 μm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.

Martino et al., "Application of the Aerial Image Measurement System (AIMS(TM)) to the Analysis of Binary Mask Imaging and Resolution Enhancement Techniques," SPIE vol. 2197, 1994, pp. 573-584.

Miller, "A New Approach for Measuring Oxide Thickness," Semiconductor International, Jul. 1995, pp. 147-148.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed., © Cambridge University Press 1988, 1992, p. 683.

O'Gorman et al., "Subpixel Registration Using a Concentric Ring Fiducial," Proceedings of the International Conference on Pattern Recognition, vol. ii, Jun. 16, 1990, pp. 249-253.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Schroder et al., Corona-Oxide-Semiconductor Device Characterization, 1998, Solid-State Electronics, vol. 42, No. 4, pp. 505-512.

Schroder, "Surface voltage and surface photovoltage: history, theory and applications," Measurement Science and Technology, vol. 12, 2001, pp. R16-R31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.

Verkuil, "Rapid Contactless Method for Measuring Fixed Oxide Charge Associated with Silicon Processing," IBM Technical Disclosure Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Volk et al., "Investigation of Smart Inspection of Critical Layer Reticles using Additional Designer Data to Determine Defect Significance," Proceedings of SPIE vol. 5256, 2003, pp. 489-499.

Weinberg, "Tunneling of Electrons from Si into Thermally Grown $SiO_2$," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 um Lithography," SPIE vol. 1604, 1991, pp. 106-117.

Huang et al., "Using Design Based Binning to Improve Defect Excursion Control for 45nm Production," IEEE, International Symposium on Semiconductor Manufacturing, Oct. 2007, pp. 1-3.

Sato et al., "Defect Criticality Index (DCI): A new methodology to significantly improve DOI sampling rate in a 45nm production environment," Metrology, Inspection, and Process Control for Microlithography XXII, Proc. of SPIE vol. 6922, 692213 (2008), pp. 1-9.

\* cited by examiner

METHODS FOR GENERATING A STANDARD REFERENCE DIE FOR USE IN A DIE TO STANDARD REFERENCE DIE INSPECTION AND METHODS FOR INSPECTING A WAFER

CROSS-REFERENCE TO RELATED APPLICATIONS

This application is a divisional of U.S. patent application Ser. No. 12/176,095 entitled "Methods for Generating a Standard Reference Die for Use in a Die to Standard Reference Die Inspection and Methods for Inspecting a Wafer," filed Jul. 18, 2008, now U.S. Pat. No. 7,796,804 issued on Sep. 14, 2010, which claims priority to U.S. Provisional Application No. 60/950,974 entitled "Methods for Generating a Standard Reference Die for Use in a Die to Standard Reference Die Inspection and Methods for Inspecting a Wafer," filed Jul. 20, 2007, which is incorporated by reference as if fully set forth herein.

BACKGROUND OF THE INVENTION

1. Field of the Invention

The present invention generally relates to methods for generating a standard reference die for use in a die to standard reference die inspection and methods for inspecting a wafer. Certain embodiments relate to a computer-implemented method for generating a standard reference die for use in a die to standard reference die inspection that includes combining output of an inspection system for a centrally located die on a wafer and one or more dies located on the wafer based on within die positions of the output.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

As design rules shrink, semiconductor manufacturing processes may also be operating closer to the limitations on the performance capability of the processes. In addition, at smaller design rules, process induced failures may, in some cases, tend to be systematic. That is, process induced failures tend to fail at predetermined design patterns often repeated many times within the design. Detection and elimination of spatially systematic, electrically relevant defects is important because eliminating such defects can have a significant overall impact on yield.

However, detection of systematic and other repeater defects using inspection techniques such as die-to-die inspection and die to standard reference die inspection are disadvantageous for a number of reasons. For example, although die-to-die inspection techniques have achieved wide spread success in wafer inspection for detection of random defects, by their very nature such inspection techniques are unable to detect systematic and repeater defects. In particular, by comparing two test die to each other, systematic and repeater defects that occur in both test die cannot be detected. In addition, die to standard reference die inspection techniques have been adopted much less than die-to-die inspection techniques in semiconductor manufacturing related applications because it is often difficult to acquire a suitable standard reference die. For example, unlike die-to-die inspection techniques in which the output for the dies that are compared is typically acquired in the same inspection scan of a wafer, die to standard reference die techniques often are complicated due to differences between the test die and the standard reference die (or the test wafer and the standard reference wafer) such as color variations and due to the difficulty in achieving relatively accurate alignment between the test die and the standard reference die.

Accordingly, it would be advantageous to develop methods for generating a standard reference die for use in a die to standard reference die inspection and methods for inspecting a wafer using die to standard die reference inspection techniques that can be used to detect repeater (systematic) defects with relatively high accuracy for applications such as single die reticle inspection and process window qualification (PWQ) applications.

SUMMARY OF THE INVENTION

The following description of various method embodiments is not to be construed in any way as limiting the subject matter of the appended claims.

One embodiment relates to a computer-implemented method for generating a standard reference die for use in a die to standard reference die inspection. The method includes acquiring output of an inspection system for a centrally located die on a wafer and one or more dies located on the wafer. The method also includes combining the output for the centrally located die and the one or more dies based on within die positions of the output. In addition, the method includes generating the standard reference die based on results of the combining step.

In one embodiment, the standard reference die includes an image. In another embodiment, the die to standard reference die inspection includes inspection for repeater defects. In an additional embodiment, the standard reference die includes substantially no noise from random defects in the centrally located die and the one or more dies. In a further embodiment, the method includes aligning the standard reference die to design data space. In one such embodiment, the generating step includes generating the standard reference die for only positions in the design data space corresponding to predetermined areas in the design data space.

In one embodiment, the output includes gray levels. In one such embodiment, the combining step includes determining a mean value of the gray levels across the within die positions. In another such embodiment, the combining step includes determining a median value of the gray levels across the within die positions. In an additional such embodiment, the combining step includes determining a mean value and a median value of the gray levels across the within die positions. In such an embodiment, the standard reference die may include the mean value across the within die positions, and the method may include generating an additional standard reference die of the median value across the within die positions. In some embodiments, the combining step includes determining a characteristic of the output across the within die positions and noise in the characteristic across the within die positions.

Each of the steps of the method described above may be performed as described further herein. Each of the embodiments of the method described above may include any other step(s) of any method(s) described herein. In addition, each of the embodiments of the method described above may be performed by any of the systems described herein.

Another embodiment relates to a method for inspecting a wafer. The method includes acquiring output of an inspection system for the wafer. The method also includes combining the output for a centrally located die on the wafer and one or more dies located on the wafer based on within die positions of the output. In addition, the method includes generating a standard reference die based on results of the combining step. The method further includes comparing the standard reference die to the output for one or more test dies on the wafer to detect defects in the one or more test dies.

In one embodiment, the standard reference die and the output for the one or more test dies include images. In another embodiment, all steps of the method are performed during run time of inspection of the wafer.

In some embodiments, the defects include repeater defects. In another embodiment, the defects include systematic defects caused by manufacturing of a reticle used to fabricate the wafer. In an additional embodiment, the defects include systematic defects, and the one or more test dies are formed on the wafer using a process window qualification (PWQ) method.

In one embodiment, the standard reference die includes substantially no noise from random defects in the centrally located die and the one or more dies. In another embodiment, the method includes combining the output for two or more of the one or more test dies such that the combined output for the two or more test dies includes less noise from random defects than the output for each of the one or more test dies. In an additional embodiment, the method includes combining the output for two or more of the one or more test dies, and the comparing step includes comparing the standard reference die to the combined output for the two or more test dies to detect the defects in the two or more test dies. In one such embodiment, the defects include repeater defects.

In one embodiment, the comparing step is performed using adaptive thresholding. In another embodiment, the comparing step includes aligning the standard reference die and the output for the one or more test dies using equalization of histograms for the standard reference die and the one or more test dies. In an additional embodiment, the comparing step includes template matching of a neighborhood of pixels in the standard reference die and a neighborhood of pixels in the output for the one or more test dies.

In one embodiment, the acquiring step includes acquiring the output for only a portion of the test dies on the wafer. In another embodiment, the method includes aligning the standard reference die to design data space. In one such embodiment, the generating step includes generating the standard reference die for only positions in the design data space corresponding to predetermined areas in the design data space.

Each of the steps of the method described above may be performed as described further herein. Each of the embodiments of the method described above may include any other step(s) of any method(s) described herein. In addition, each of the embodiments of the method described above may be performed by any of the systems described herein.

An additional embodiment relates to another method for inspecting a wafer. This method includes acquiring output of an inspection system for a standard reference wafer. The method also includes combining the output for a centrally located die on the standard reference wafer and one or more dies located on the standard reference wafer based on within die positions of the output. In addition, the method includes generating a standard reference die based on results of the combining step. The method further includes acquiring output of the inspection system for the wafer. Furthermore, the method includes comparing the standard reference die to output for one or more test dies on the wafer to detect defects in the one or more test dies.

In one embodiment, the defects include repeater defects. In another embodiment, the defects include systematic defects caused by manufacturing of a reticle used to fabricate the wafer. In an additional embodiment, the defects include systematic defects, and the one or more test dies are formed on the wafer using a PWQ methodology.

In some embodiments, the standard reference die includes substantially no noise from random defects in the centrally located die and the one or more dies. In another embodiment, the method includes combining the output for two or more of the one or more test dies such that the combined output for the two or more test dies includes less noise from random defects than the output for each of the one or more test dies. In an additional embodiment, the method includes combining the output for two or more of the one or more test dies, and the comparing step includes comparing the standard reference die to the combined output for the two or more test dies to detect the defects in the two or more test dies. In one such embodiment, the defects include repeater defects.

In one embodiment, the method includes aligning the standard reference die to design data space. In one such embodiment, the generating step includes generating the standard reference die for only positions in the design data space corresponding to predetermined areas in the design data space. In another embodiment, the method includes determining a position of the standard reference die and a position of the output for the one or more test dies with respect to design data space prior to the comparing step and aligning the standard reference die and the output for the one or more test dies based on the positions of the standard reference die and the output for the one or more test dies with respect to the design data space prior to the comparing step.

In one embodiment, the method includes aligning the standard reference die to the output for the one or more test dies prior to the comparing step using a frame by frame alignment technique. In another embodiment, the method includes aligning a first swath of the output for the one or more test dies with respect to a global alignment and aligning a second swath of the output for the one or more test dies to the first swath to thereby align the second swath to the global alignment.

In one embodiment, the comparing step is performed using adaptive thresholding. In another embodiment, the comparing step includes aligning the standard reference die and the output for the one or more test dies using equalization of histograms for the standard reference die and the one or more test dies. In an additional embodiment, the output of the inspection system for the wafer includes at least two samples per illumination spot on the wafer.

In one embodiment, acquiring the output of the inspection system for the wafer includes acquiring the output for only a portion of the test dies on the wafer. In another embodiment, acquiring the output for the standard reference wafer and the wafer is performed using broadband deep ultraviolet mode inspection. In an additional embodiment, acquiring the output for the standard reference wafer and the wafer is performed using broadband edge contrast mode inspection. In some embodiments, acquiring the output for the standard reference wafer and the wafer is performed using electron beam inspection.

Each of the steps of the method described above may be performed as described further herein. Each of the embodiments of the method described above may include any other step(s) of any method(s) described herein. In addition, each of the embodiments of the method described above may be performed by any of the systems described herein.

A further embodiment relates to a computer-implemented method for detecting defects on a wafer. The method includes combining multiple images of a structure formed on the wafer to generate a composite image of the structure. The multiple images are acquired at multiple positions on the wafer at which the structure is formed. The method also includes comparing the composite image to a reference to detect defects on the wafer.

In one embodiment, the defects include systematic defects. In another embodiment, the defects have a size that is approximately equal to line edge roughness of the structure.

In one embodiment, the combining step includes averaging the multiple images. In some embodiments, the multiple positions include positions of the structure in cells having identical designs. In another embodiment, the multiple positions include positions of the structure in neighboring dies.

In one embodiment, the combining step is performed such that the composite image has less line edge roughness than each of the multiple images. In another embodiment, the combining step is performed such that the composite image has less random variation than each of the multiple images. In an additional embodiment, the combining step is performed such that the composite image has less gray level noise than each of the multiple images.

In one embodiment, the reference includes a known good image of the structure. In another embodiment, the reference includes an image of the structure acquired in a standard reference die. In an additional embodiment, the reference includes a reference image, a composite test image, or a reference and a composite test image of the structure acquired in a process window qualification die. In a further embodiment, the reference includes a rendered database image. In some embodiments, the reference includes a composite image of the structure generated from multiple images acquired at multiple positions on the wafer or on a different wafer.

Each of the steps of the method described above may be performed as described further herein. Each of the embodiments of the method described above may include any other step(s) of any method(s) described herein. In addition, each of the embodiments of the method described above may be performed by any of the systems described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
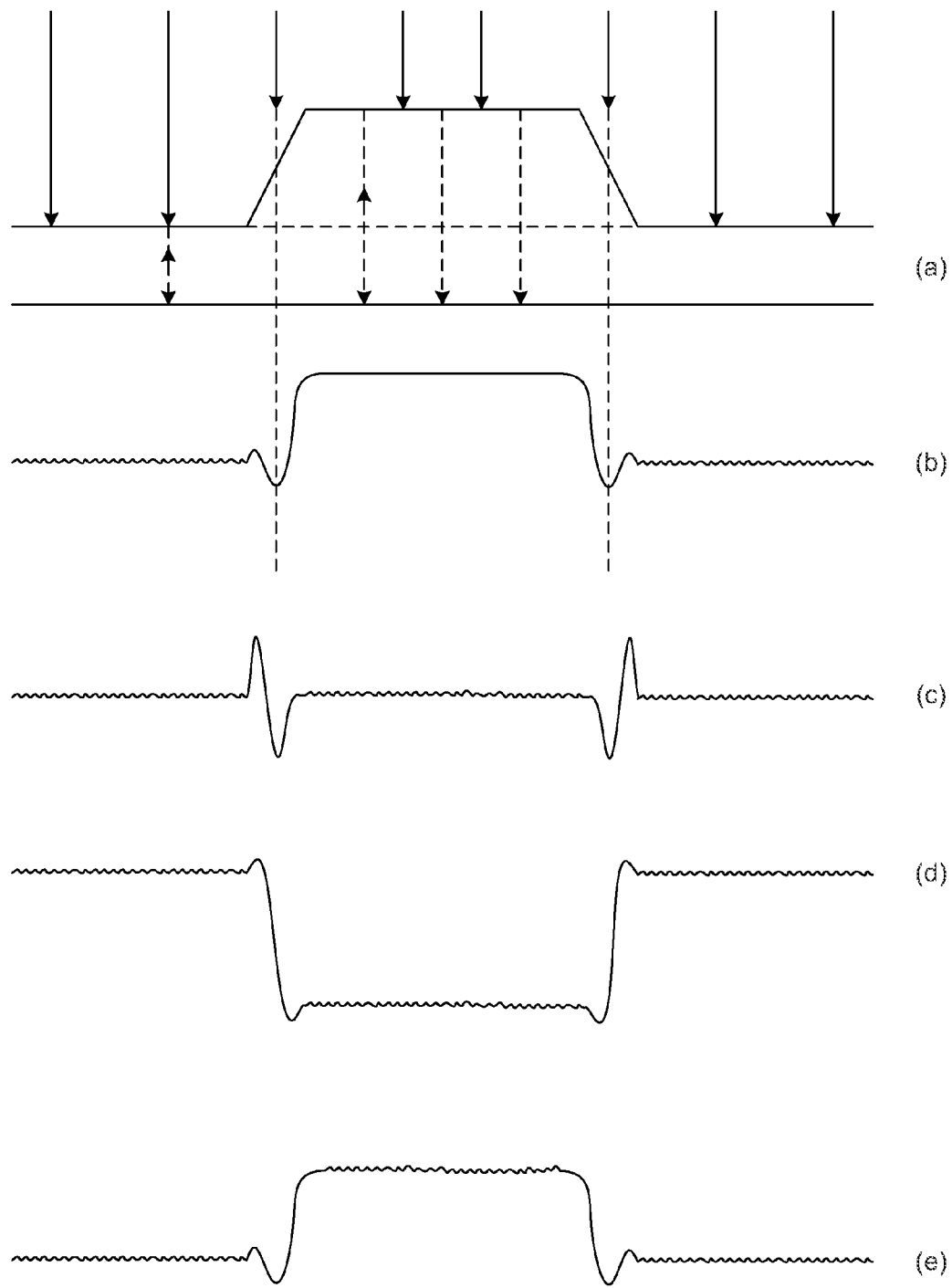
FIG. 1 is a series of plots illustrating the phase contrast effects of a single layer of material on a square wave function in narrow band bright field imaging.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits (ICs) may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

The embodiments described herein are generally based on new ways of thinking about algorithmic approaches for systematic (repeater) defects. Recently, inspection system customers have begun to request that inspection systems include a "standard reference die feature" that can be used to detect systematic or repeater defects. Such requests have grown out of concerns about crystal growth defects on reticles, which when they become printable cause repeater defects on wafers. If the reticle is a single die reticle, traditional die-to-die inspection approaches cannot detect such defects as there is no reference comparison die. The most sensitive approach for detecting such crystal growth defects would naturally be to inspect the reticle using reticle inspection systems configured for inspection using both reflected and transmitted light, and such reticle inspection systems are commercially available from KLA-Tencor, San Jose, Calif. In addition, the frequency of reticle inspection using such systems may be increased to detect the crystal growth defects relatively soon after formation thereby reducing the adverse effects of such defects on wafer fabrication.

However, there still remains demand for a standard reference die inspection approach (in which a known good standard reference die is stored and then compared with the sample). In addition, although there is currently not widespread demand for such an inspection approach (e.g., perhaps due to relatively heavy adoption of the reflected and transmitted light based reticle inspection systems and/or limited use of relatively expensive single die reticles), there is enough demand for standard reference die inspection to warrant development of an effective solution. Furthermore, a new approach to standard reference die based inspection is desirable since previously used standard reference die based inspections typically lack the sensitivity of traditional die-to-die comparisons due to process noise differences between the reference wafer and the test wafer.

Standard reference die based inspection methods are particularly useful for detecting repeater (systematic) defects. In addition, using a bright field (BF) inspection system for after develop inspection (ADI) to detect repeater defects in situ is desired such that lots of wafers are not allowed to pass through fabrication with zero yield on wafers printed using high end single die reticles. Another driving force for performing standard reference die based inspection of wafers is that by inspecting for repeater defects on wafers only repeater defects that have printed on the wafers will be detected. In contrast, by inspecting a reticle for potential repeater defects, repeater defects that will and will not print on wafers will be detected. Furthermore, inspecting at ADI allows re-working of the wafers if necessary.

Standard reference die based inspection would also be advantageous for process window qualification (PWQ) methods in that a standard reference die generated using output acquired for product wafers can be used to detect systematic defects that occur due to shrinking process window margins. However, when catastrophic process window margin conditions occur, the weakest design in the die will collapse. Unfortunately, not only is the signal weak for such defects, but if such defects repeat, they are effectively a single die repeater problem.

There are different types of repeater defects. For example, repeater defects may include hard repeater defects, soft repeater defects, and marginal repeater defects. Hard repeater defects are defined herein as defects that occur at approximately the same die location in a majority (e.g., greater than about 50%) of the inspected dies. Soft repeater defects are defined herein as defects that occur at approximately the same die location in a significant minority (e.g., about 15% to about 50%) of the inspected dies. All other types of repeater defects are treated herein as random defects (the marginal repeater defects). Random defects may be defined somewhat arbitrarily and may vary depending on the defect, the location of the defect, the number of dies in which the defect is detected, and the process being performed on the wafer. For example, inspection of 100 dies on a wafer may identify a defect that repeats in 10 of the dies as significant.

In the context of crystal growth defects, a situation often occurs in which crystal growth has in fact occurred (typically in open areas of the reticle) but has a relatively low opacity and as a result does not print on the wafer. At some other point, crystal growth defects start printing and may be relatively low occurrence defects on the wafers (but may show up on say every die), or they may sporadically occur (soft repeaters) due to, for example, a threshold issue (in the threshold used to detect defects). In such situations, one approach may be to link reticle inspection systems in the fab (e.g., reflected and transmitted light based reticle inspection systems) with defect review and/or inspection systems (e.g., electron beam based defect review and/or inspection systems). In this manner, output of a reticle inspection system and a defect review system may be used to determine if repeater defects on the reticle are printing on the wafer and if the wafer inspection systems are not detecting the defects. For example, a short loop review inspection cycle optimization (RICO) type experiment may be performed between the wafer inspection system and the defect review and/or inspection system (e.g., a scanning electron microscope (SEM)).

Traditional defect detection approaches are typically centered around a number of factors. One such factor is maximizing the signal (e.g., optical photons). Another factor is minimizing the system noise (e.g., shot noise, die-to-die alignment noise, distortion noise, etc.). In addition, another factor is minimizing the wafer process noise (e.g., color noise, grain noise, previously layer noise, etc.). Traditional defect detection approaches are also typically based on double detection schemes in which the test sample is compared with at least two references. Some defect detection approaches also attempt to reduce the noise (variance) on the reference (e.g., reduce noise in the reference by the square root of noise (n) (sqrt (n)) by using an algorithm such as multiple die auto-thresholding (MDAT)). In addition, some defect detection approaches attempt to bin the defects when possible, for example, to reduce false alarms and to aid in defect review (e.g., SEM) sampling. Furthermore, defect detection approaches tend to attempt to maximize the throughput on a per wafer basis (e.g., for random defect detection, some approaches attempt to inspect between one to two wafers in less than one hour such that SEM review can be performed in another hour so that the lot is not held for more than two hours). In addition, the above factors may vary depending on the application for which inspection is being used (e.g., different factors may be used for creating inspection approaches for electrical analysis (EA) and line monitoring (LM)).

Some wafer inspection systems are advantageously designed to detect a critical defect type that is well below the resolution limit of the optics of the inspection system. To achieve such detection, the signal-to-noise ratio (S/N) of output of the optics is typically maximized. Some approaches to maximizing the S/N may include designing front end algorithms to increase the S/N. Other approaches include attempting to create substantially the same pattern aliasing between the test and reference wafers (e.g., using the run time alignment (RTA) feature developed by KLA-Tencor), to maximize the optics, apertures, etc., to maximize the potential defect signal, and to use numerous algorithms to minimize color and grain noise.

However, these factors may not necessarily impact or determine the ability of inspection systems to detect repeater defects. For example, one factor that may detract from repeater defect detection is that the statistics used for detecting and binning random defects are based on detecting essentially solitary events. While noise can be reduced in the reference signal (thereby "cleaning up the reference signal"), no such device, algorithm, or method exists for solitary event detection. For example, some approaches for detecting defects below the resolution of the optics tend to involve turning up the sensitivity to the noise floor (which is typically limited by wafer processing induced noise) and then adjusting the algorithms and optics used for inspection so that a defect signal can emerge from the overall signal and be detected. However, in contrast to random defect detection, if the location of a repeater defect is known, then a lot more options become available for enabling defect detection.

A number of characteristics of repeater defects can be exploited to increase the detection sensitivity. Two categories that are considered here include reticle induced repeater defects (in the fab) and PWQ type systematic catastrophic repeater defects. Reticle repeater defects occur either due to particles on the reticle that get exposed as pattern or the above-mentioned crystal growth. Crystal growth defects typically first occur in clear areas of the mask (that get exposed), often starting from the edges of the reticles and have an appearance on the reticle that looks like haze. However, once crystal growth defects start printing on wafers, the crystal growth defects could either be well exposed thereby causing a relatively clear end of line (EOL) failure or sometimes occur as a reliability failure by causing weak opens (large resistance but not a complete open). In addition, because crystal growth is a global phenomenon on reticles (even though the entry points may be at the edge), multiple occurrences will typically happen. Of course, the challenge is to compare the output for a wafer being inspected with a standard reference. Another characteristic of repeater defects that can be exploited will be that even though the geometry of the defect repeats, it is highly unlikely to be man made (e.g., have linear, Manhattan type geometries). The latter characteristic can be exploited by shape based binning and classification algorithms. Training for binning and classification in this case can be performed based on a priori wafers on which the problem occurs, which is not something that can usually be performed with truly random defects.

PWQ type repeater defects differ from the reticle repeater defects described above in that they typically affect the most delicate structures (e.g., the weakest pattern). If total collapse occurs, a clear open or short may occur. However, more often than not pattern movement may be the issue. Therefore, detecting PWQ type defects using a standard reference type image requires positional fidelity (e.g., sub-pixel alignment to design data). Another factor that is different for such defects is that ultimately a lot of PWQ defects occur where the geometry size is the smallest ("tightest") and therefore signal contrast is potentially substantially low. Also, the defect geometry of PWQ type defects, unlike the geometry of reticle repeater defects, does more often than not look like patterned features (or the lack thereof). Defects that appear in this manner can be a bit hard to distinguish from system alignment errors. Lastly, much like reticle repeater defects, the prospect for a priori spots where such events occur is quite promising. Such spots may be determined using, for example, Design-Scan analysis software that is commercially available from KLA-Tencor, methods for evaluating reticle layout data such as those described in commonly owned U.S. patent application Ser. No. 11/226,698 by Verma et al., filed Sep. 14, 2005, published as U.S. Patent Application Publication No. 2006/0062445 on Mar. 23, 2006, which is incorporated by reference as if fully set forth herein, design based binning (DBB), which may be performed as described in commonly owned U.S. patent application Ser. No. 11/561,659 by Zafar et al., filed Nov. 20, 2006, published as U.S. Patent Application Publication No. 2007/0288219 on Dec. 13, 2007, which is incorporated by reference as if fully set forth herein, and other design for manufacturing (DFM) hot spot sources. The embodiments described herein may include any step(s) of any method(s) described in these patent applications.

Virtually all of the above factors affect repeater defect detection. However, if an additional constraint is that the defects of interest only include repeater defects and not random defects, a different set of emphases can arise. For example, when random defects (often as the primary defect type) are to be detected in addition to repeater defects, then repeater defect detection is essentially the same exercise with some caveats. In particular, inspection of single die reticle printed wafers for repeater defects cannot be performed. In addition, repeater defect detection may essentially be a software stacking exercise in that there is not an inherent signal or image processing enhancement available over and above what is performed for random defect detection.

ADI inspection has traditionally been somewhat under-adopted due to issues with previous layer noise. For example, previous layer noise may be relatively significant in inspection for layers such as trench etch, ADI layers, and shallow trench isolation (STI) layer inspection after chemical-mechanical polishing (CMP). Although, as more issues arise in lithography steps, ADI inspection is being used more to monitor and control such issues. The use of ADI resist layer inspection is also different for fabrication of different devices. For example, ADI resist layer BF inspection may account for a larger percentage of the inspections performed for logic fabrication compared to memory fabrication.

There are a number of currently available optical approaches for ADI layer inspection. For example, there are number of different spectral modes that can be used for ADI inspection of resist layers for both full loop (complete build of devices on the wafers) and short loop (partial build of the devices on the wafers). Examples of such spectral modes include deepband, blueband, GHI line, G line, and broadband (BB) deep ultraviolet (DUV). Typically, a majority (about 90%) of resist layer ADI inspections are performed in the DUV spectral region. In addition, different imaging modes such as edge contrast (EC) mode (in which complementary apertures are used in the illumination and imaging paths) and BF mode are used for resist layer ADI inspections for the full loop and the short loop. In general, although EC mode and BF mode are used for many different resist layer ADI inspections, EC mode may be used more often than BF mode.

The greater reliance on BB DUV EC mode described above (and, when possible, UV dark field (DF) inspection systems such as the Puma series of tools that are commercially available from KLA-Tencor) may be due at least in part to the previous layer noise issues. However, if previous layer noise (due to previous layer defects) can be easily removed (e.g., using algorithms), BF BB DUV inspection may be used instead of EC mode inspection. Examples of methods that can be used to remove previous layer noise are illustrated in commonly owned U.S. patent application Ser. No. 11/533, 079 by Ramani et al., filed Sep. 19, 2006, which is incorporated by reference as if fully set forth herein. The embodiments described herein may include any step(s) of any method(s) described in this patent application. Using BF BB DUV mode inspection may help with inspection in terms of resolution though color noise considerations should also be balanced. In addition, as described further herein, the embodiments described herein may allow scan times to be an order of magnitude slower than for traditional random defect inspection (e.g., using specialized repeater defect inspection focused on only a few die). Scanning at half speed or quarter speed may be quite appropriate, but the usual precautions in terms of dosage should be taken into account (e.g., such that the dosage does not approach levels that may cause damage to the wafer or materials formed thereon).

The optical signal used for random defect detection may also be altered to enhance repeater defect detection. For example, optics selection is becoming more complicated for inspection of sub-wavelength features. However, optics that are different from those used for conventional approaches to random defect detection may not be necessary although that may be determined using wafers on which defects are formed. However, some of the basic factors such as intensity (energy), resolution (e.g., numerical aperture (NA)), contrast (e.g., modulation transfer function (MTF)), modes (apertures, EC, etc.), and spectrum may be explored to determine if they affect detection of repeater defects.

When considering the energy factor, one factor that may be in favor of repeater defect detection is that in standard reference die inspection, the user does not really want to inspect the entire wafer. In fact, assuming (for good reasons as described further herein) that inspecting five dies is sufficient and the time allowed for inspection is about one hour, five dies can be inspected in under five minutes. Therefore, the remaining time allowed for inspection presents a lot of opportunities optically (possibly computationally as well). For example, scanning may be performed slower to allow more light to be collected and detected. However, scanning at a slower speed results in exposing the wafer to increased amounts of light, and the materials on the wafer may affect how much light to which the wafer can be exposed without adverse changes in the materials. In addition, scanning may be performed more slowly in relatively high NA EC mode, which is typically "light starved." Furthermore, multi-pass inspection (such as BF and EC combined) may be performed in the remaining allowed time. Therefore, these factors may be explored to determined a system-based solution that leverages the context.

In some embodiments, the output of the inspection system may include output acquired using an electron beam inspection system. The electron beam inspection system may include any suitable electron beam inspection system known in the art. In electron beam inspection, lower beam currents may be used, which allows improved resolution albeit at lower throughput. Alternatively, various averaging techniques such as pixel averaging, line averaging, or frame imaging may be used to reduce noise at lower effective scan speeds.

While inspection may be performed for repeater defects at the highest resolution or the mode that provides the most contrast, many wafer inspection systems are configured to detect defects without resolving them. However, resolution typically should be sufficient such that the defect(s) in question can perturb the nominal background sufficiently to produce a contrast. Therefore, as high a resolution as possible may be desirable but not necessarily at the cost of reduced contrast or increased aliasing errors due to misalignment. For example, increasing the NA of the optics may increase the resolution of the inspection system, but may also increase the misalignment errors unless such errors are corrected prior to digitization. In addition, unlike random defect detection, for an application like standard reference die inspection, the misalignment effects should be considered. In general, the alignment positioning will be potentially several pixels off, and after correcting for coarse errors, the worst case misalignment errors may still be about one half of a pixel, which can produce the maximum aliasing error. One way to optically mitigate this effect is to use more spots per point spread function (PSF) (e.g., roughly at least 3.5 pixels) or more empty magnification. In this situation, a more gradual rise time on the edges may be used (e.g., by optical low pass filtering or lower effective spatial frequency bandwidth).

In this manner, standard reference die based inspection described herein may be performed with oversampling. For such inspection, oversampling may be any sampling greater than the Nyquist criteria of 2 samples per spot. Oversampling is typically avoided because it reduces the throughput of the inspection process. However, as described further herein, only a portion of the wafer may be inspected for standard reference die based inspection thereby reducing the throughput concerns caused by oversampling. However, excessive oversampling is preferably avoided such that the sampling does not introduce aliasing effects.

Another way to enhance contrast is to exploit the phase contrast or thin film effects that may be caused by materials on the wafers. Phase contrast enhancement usually comes with significant downsides such as increased nuisance defect detection since any changes in film thickness may cause variations in intensity. The big issues for using phase contrast enhancement for repeater defect detection applications are the type of phase differences one would have between a reference and test wafer. However, the color (process) noise level for the same die on different wafers may be approximately the same. In addition, in general, dies located toward the center of the wafer tend to be relatively well controlled in terms of process noise. Therefore, the basic strategy for standard reference die inspection can be relatively simple. In particular, the center die row (e.g., five to eight dies in the center die row) may be used for both creating the standard reference die as well as the test die. There will always be residual color variations, and those color variations may be dealt with algorithmically. In this manner, the various effects of color variation could be simplified as possible.

Considering a narrow band (NB) imaging mode and a single layer stack of material, the single layer of material will effectively act as a quarter wave plate. Therefore, phase contrast effects of the single layer of material on a traditional near square wave edge as shown in FIG. 1(a) could produce the responses shown in FIG. 1 for BF imaging. In particular, FIG. 1(b) shows the simple step-like function (with 0 degrees phase retardation) that could become an impulse-like function as shown in FIG. 1(c) with 90 degrees phase retardation to total contrast reversal as shown in FIG. 1(d) with 180 degrees phase retardation and something where the contrast is diminished as shown in FIG. 1(e) with 45 degrees phase retardation.

Figure 2:
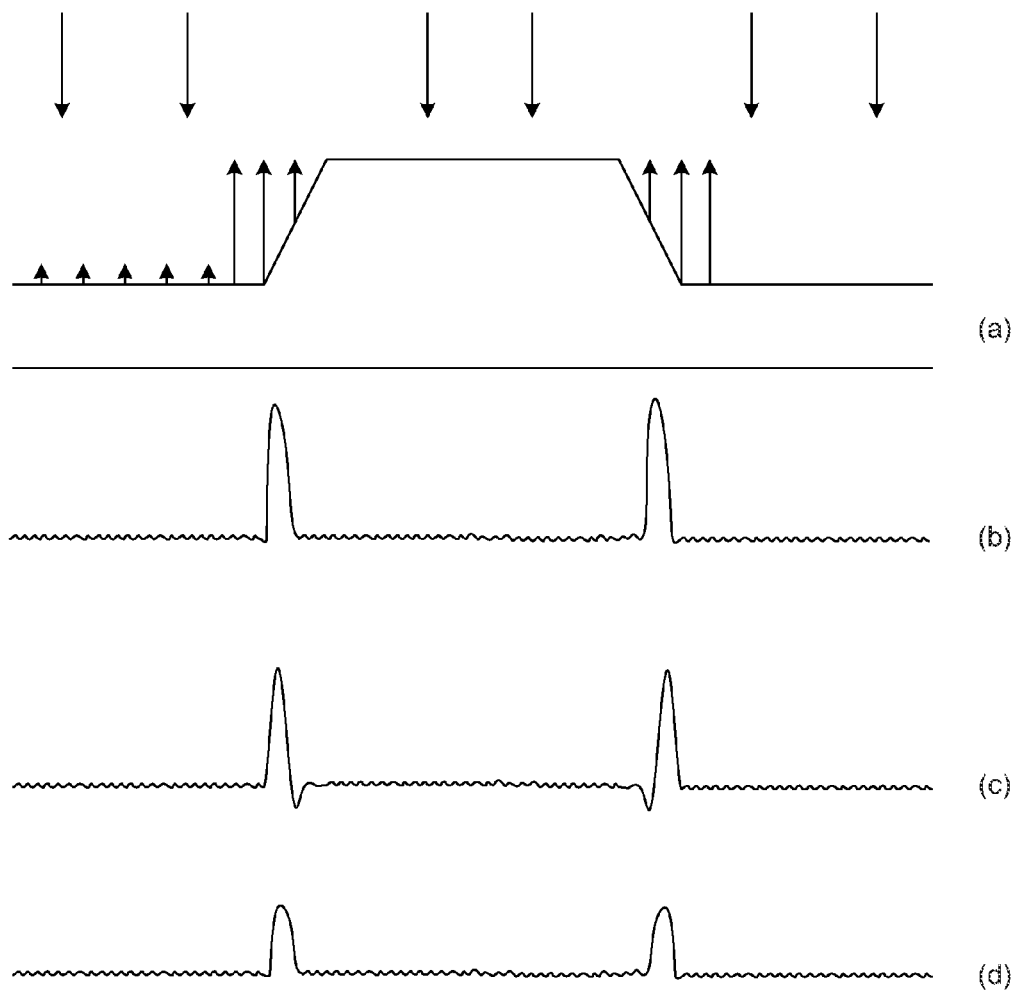
FIG. 2 is a series of plots illustrating the phase contrast effects of a single layer of material on a square wave function in narrow band edge contrast mode imaging.

The same near square wave edge is shown in FIG. 2(a), and FIGS. 2(b), 2(c), and 2(d) show the phase contrast effects of the single layer of material on the near square wave edge in NB EC mode imaging. In particular, FIG. 2(b) shows the simple step-like function (with 0 degrees phase retardation) that could become a function such as approximately that shown in FIG. 2(c) with 90 degrees phase retardation to a function such as approximately that shown in FIG. 2(d) with 180 degrees phase retardation. EC mode effectively produces scattering only from the edge of the near square wave, which effectively acts like an optical first derivative of the BF image. As shown in FIG. 2, therefore, EC mode may change the amplitude of the output corresponding to the edges in response to film thickness changes. NB EC mode may not be completely immune to color and previous layer signals since there may be some background scattering from prior layers that is allowed to pass through the EC imaging aperture. In addition, film thickness changes probably will scatter differently from the edges, and therefore edge amplitudes may change. Phase contrast issues are seen much more in back end layers as opposed to front end layers (e.g., due to more film stack instability).

The basic approaches to mitigating these effects may be to broaden the spectrum and use EC mode. In both cases, the resolution (MTF) may be decreased. However, as described further herein, the wafer-to-wafer alignment issues must also be dealt with. To mitigate the wafer-to-wafer alignment issues without using an active RTA system, more samples per spot (or a relatively lower NA for a given pixel size) may be used. In this manner, oversampling may be used to overcome the alignment issues.

Currently used repeater defect detection approaches for BF typically utilize basically A-B, B-C comparison techniques. In the typical case, A and C are used as the reference dies, and B is used as the test or candidate die in which defects are being detected. This type of inspection approach attempts to maximize the ability to capture single isolated signals that are seen as distinct events above a certain threshold for both pairs of comparison. A more refined version of this comparison may be performed using the MDAT algorithm, which attempts to create a perfect reference for comparison. In this approach, the reference dies A and C are actually the average or median values of a set of about five dies to about eight dies centered around die A or C, respectively (although the actual implementation may vary). Since BF systems tend to have an RTA subsystem that delivers sub-pixel accuracy, die-to-die aliasing errors of less than 0.1 pixel are minimized, and excellent performance may be achieved for pixels with relatively large sample spots. There is also a fine image alignment step that further attempts to minimize these errors (e.g., to less than about 0.01 pixel) using a more sophisticated interpolation scheme. The selection of the threshold itself may be performed in a number of ways but most tend to use a form of adaptive thresholding based on the context of the neighborhood. Such approaches are quite successful in minimizing global color variation. However, there remains the question of how accurately the region was labeled in the first place (e.g., due to segmentation error), the population size, etc. The MDAT algorithm is quite sophisticated in this regard. As such, the MDAT algorithm may be algorithm of choice to start with.

The basic limitation of detecting repeater defects is that in the single die reticle (SDR) case, a repeater defect cannot be distinguished from the pattern. In the case of weak repeaters in a SDR, only a substantially weak repeater will be detected. In fact, the weak repeater may be so weak (in the sense that it occurs only randomly) that it is effectively detected as a random defect. Such defects may be determined to be potential repeater defects by stacking output for multiple dies across the entire wafer. The situation is clearly better in the case of multiple die reticle (MDR) induced defects in which the reticle includes a natural reference (e.g., one of the multiple dies). However, again the detection of repeater defects for MDR is really not optimal. For example, if the signal is relatively low to start with, then there is no easy way to amplify the signal. Obviously, previous layer defect noise complicates this approach.

Based on the above considerations, an algorithm for standard reference die comparison for repeater defect detection may be created. In particular, the embodiments described herein provide a comprehensive inspection strategy that not only enables repeater (systematic) defect detection but may also optimize repeater defect detection. The embodiments described herein may be used as another "pass" or mode in wafer inspection like the array modes and random modes. For example, the embodiments described herein may be implemented using existing wafer inspection systems or other existing systems possibly with suitable changes in configuration as described further herein. In this manner, the embodiments described herein embrace and enable standard reference die based inspection, which is the most effective method for detecting systematic defects.

One embodiment relates to a computer-implemented method for generating a standard reference die for use in a die to standard reference die inspection. In one embodiment, the die to standard reference die inspection includes inspection for repeater defects, which may be performed as described further herein. The repeater defects may include any of the repeater defects described herein.

Figure 3:
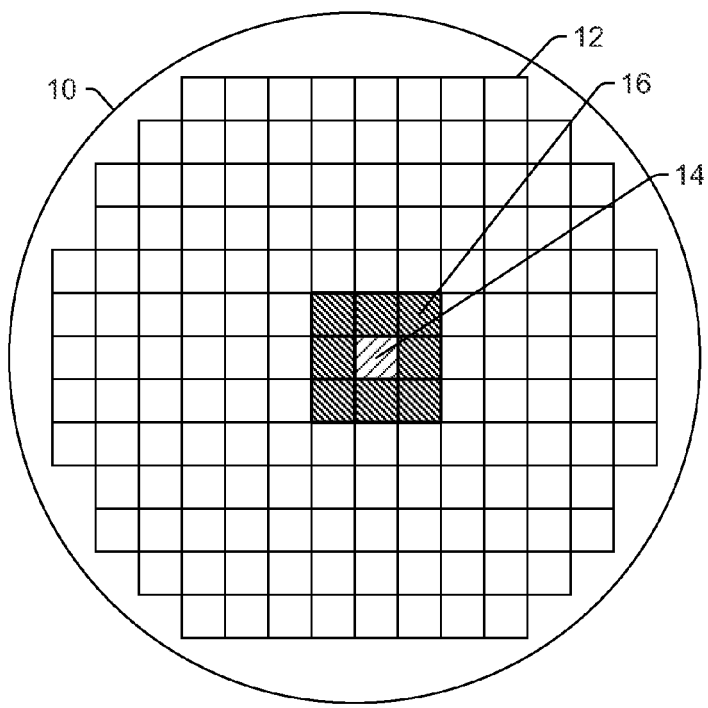
FIG. 3 is a schematic diagram illustrating a top view of one embodiment of a centrally located die on a wafer and one or more dies located on the wafer.

The method includes acquiring output of an inspection system for a centrally located die on a wafer and one or more dies located on the wafer. In some embodiments, the one or more dies are located adjacent to the centrally located die. One embodiment of such dies is shown in FIG. 3. For example, as shown in FIG. 3, wafer 10 includes array 12 of dies formed on the wafer including centrally located die 14 and dies 16 located adjacent to the centrally located die. As shown in FIG. 3, the centrally located die is not located at exactly the center of the wafer. In other words, the center of the centrally located die does not coincide with the center of the wafer. Instead, in this embodiment, the centrally located die is located near the center of the wafer (e.g., one edge of the centrally located die is located at approximately the center of the wafer). The centrally located die may be selected to be any of the dies located near the center of the wafer particularly in instances such as that shown in FIG. 3 in which the center of the wafer coincides with a space between dies in the array. However, the centrally located die may be positioned at the center of the wafer.

Acquiring the output may include using an inspection system to acquire the output for the centrally located die on the wafer and the one or more dies on the wafer, for example, by scanning the wafer with light and detecting light reflected or scattered from the wafer. In this manner, acquiring the output for the centrally located die and the one or more dies on the wafer may be similar to performing an inspection of the portion of the wafer including those dies. The inspection system may be configured as described herein. Alternatively, acquiring the output may include acquiring the output from an inspection system used to generate the output. For example, the method may include acquiring the output from a storage medium in which the inspection system stored the output. The storage medium may include a storage medium of the inspection system, a storage medium such as a fab database, a storage medium configured as described herein, any other storage medium coupled to the inspection system, or any other suitable storage medium known in the art. In this manner, acquiring the output for the centrally located die and the one or more dies on the wafer may not include inspecting the wafer. In addition, output of the inspection system may be acquired for the entire wafer while only the output for the centrally located die and the one or more dies located on the wafer may be used to generate the standard reference die.

The simplest implementation of the acquiring step described above is to inspect the central die row of the wafer and then create a standard reference die image centered around the central die (or two). In some embodiments, output acquired for at least five dies may be used to create the standard reference die. Using MDAT suggests that eight dies may be a good number of dies. However, if output acquired for too many dies is used to create the standard reference die, color variations in the wafer may become pronounced in the standard reference die since the color variations tend to become pronounced near the outer edge of the wafer. In one embodiment, output acquired for nine dies (in a three die by three die arrangement) in or near the center of the wafer may be used to create the standard reference die.

The output acquired for the centrally located die and the one or more dies on the wafer may include output in any suitable format known in the art. In one embodiment, the standard reference die includes an image. In this manner, the methods described herein may include creating a standard reference die image. In one such embodiment, the inspection system that generated the output for the centrally located die and the one or more dies on the wafer may be configured as an image based inspection system.

The method also includes combining the output for the centrally located die and the one or more dies based on within die positions of the output. In other words, output acquired at the same within die position for the centrally located die and the one or more dies may be combined. The output acquired at the same within die position for multiple dies may be identified by aligning the output acquired for the multiple dies to each other. In addition, the output acquired at the same within die position for multiple dies may be identified by determining the within die position of the output (e.g., using some common reference or coordinate system). Such alignment or determining the within die position may be performed as described further herein. In this manner, there may be some significant implementation difficulties if dies that are not scanned together are averaged or otherwise combined. One interesting artifact to consider is whether or not to use RTA for the embodiments described herein. Alignment will be described further herein. For now, RTA can be assumed to be used.

In one embodiment, the output includes gray levels. In one such embodiment, the combining step includes determining a mean value of the gray levels across the within die positions. The mean values may be determined using any suitable algorithm and/or method. In another such embodiment, the combining step includes determining a median value of the gray levels across the within die positions. The median value may be determined using any suitable algorithm and/or method. In a further such embodiment, the combining step includes determining a mean value and a median value of the gray levels across the within die positions. The mean values and the median values may be used to create two different standard reference dies. For example, in one such embodiment, the standard reference die includes the mean value across the within die positions, and the method includes generating an additional standard reference die of the median value across the within die positions.

In some embodiments, the combining step includes determining a characteristic of the output across the within die positions and noise in the characteristic across the within die positions. In these embodiments, the characteristic of the output may include any of the characteristics described herein (e.g., mean, median, etc.). In addition, the noise in the characteristic may be determined as described further herein.

The method further includes generating the standard reference die based on results of the combining step. For example, generating the standard reference die may include storing one or more attributes of the standard reference die. The most logical (well behaved linearly) value to store is the mean value of the gray level. The next candidate is the median of the gray level, which will preserve the sharpness better than the mean value but may also create some interesting non-linear artifacts. The fact that MDAT has successfully used the median suggests that median value should be the leading candidate for the embodiments described herein.

Information about the noise in the surroundings may also be stored. The logical pairing of a noise attribute for mean would be the standard deviation, with median perhaps the range. Storing an additional attribute for noise in the standard reference die would require an additional eight bits. Since range in particular may be substantially noisy with alignment errors, a smoothing neighborhood may be used in the embodiments described herein. On the other hand, it may be valuable to know if the output used to generate the standard reference die is in a particularly noisy area. In some embodiments, the additional attribute for noise may be used as a control on the thresholds used for defect detection. In addition, or alternatively, the additional attribute for noise may be used as a comparison vector for defect detection.

In one embodiment, the standard reference die includes substantially no noise from random defects in the centrally located die and the one or more dies. For example, in some embodiments, the method may include reducing random defects in the standard reference die and/or identifying susceptible pixels in the standard reference die. For example, the method may include determining how good the wafer is (e.g., how defect free the wafer is). Determining how good the wafer is as a reference may include performing defect review of the centrally located die and the one or more dies based on the output acquired for these dies. In addition, by combining the output of two or more dies as described above to create the standard reference die, the noise in the standard reference die is effectively reduced (e.g., by averaging) while non-noise signals are effectively amplified (e.g., by averaging). For example, the process of averaging data from N die will amplify the signal by v n. Median is probably a better attribute in that it will most likely eliminate any vestige of a previous layer or random defect. The embodiments described herein may also include storing the difference between the median and the average as a measure of the noise in the pixels. However, as described above, the method may also include storing a 16 bit value (effectively 2 images): one with mean and the other with median. These steps may be performed with some degree of simulation and experimentation using real wafers.

In one embodiment, the method includes aligning the standard reference die to design data space. In one such embodiment, the generating step includes generating the standard reference die for only positions in the design data space corresponding to predetermined areas in the design data space. The predetermined areas may include, for example, areas in the design data corresponding to critical areas of the design, care areas of the design (or areas that the user "cares" about), hot spots in the design, etc. The predetermined areas may be determined in any suitable manner as described further herein. In addition, the predetermined areas may be determined by the embodiments described herein or by another system or method.

In this manner, in some embodiments, a system of systems approach may be used for creating the standard reference die. In one such example, a known "good" standard reference die may be created using reticle inspection systems. In another example, the output acquisition and/or processing of the acquired output used to create the standard reference die may be trained on a hot spot generated sample plan. The hot spot generated sample plan may be generated in a number of manners included DesignScan, DBB, etc. For example, context based inspection (CBI) methods generally use information about design data to inspect portions of the wafer in which important design data is printed but not portions of the wafer in which unimportant design data is printed. In other words, CBI may use the context of the design data to perform targeted or "smart" inspection. In one such example, design data may be used during inspection to detect defects only in relatively sensitive areas of the design data. For example, output of inspection of a wafer such as an image may be stored, and only portions of the image corresponding to sensitive areas of the design may be compared to detect defects in the portions of the image. As such, the standard reference die may be created to include only portions of the die that will be inspected. For example, the design data may be used to determine which portions of the test die will be inspected in CBI of the wafer, and the standard reference die may be created to include only portions of the die corresponding to the portions of the test die that will be inspected. Therefore, the standard reference die created in the embodiments described herein may be a relatively sparse standard reference die, which may advantageously reduce the storage requirements for the standard reference die. In this manner, in one implementation, standard reference die inspection may include image and context based inspection. In addition, standard reference die inspection and image and context based inspection may be performed simultaneously or sequentially.

Another embodiment relates to a method for inspecting a wafer. The method includes acquiring output of an inspection system for the wafer. The acquiring step may be performed as described herein. The method also includes combining the output for a centrally located die on the wafer and one or more dies located on the wafer based on within die positions of the output. The combining step may be performed as described herein. In addition, the method includes generating a standard reference die based on results of the combining step, which may be performed as described herein. The standard reference die may be configured as described herein. For example, in one embodiment, the standard reference die includes substantially no noise from random defects in the centrally located die and the one or more dies. In another example, in some embodiments, the method includes aligning the standard reference die to design data space, and the generating step includes generating the standard reference die for only positions in the design data space corresponding to predetermined areas in the design data space. These steps may be performed as described further herein.

The method further includes comparing the standard reference die to the output for one or more test dies on the wafer to detect defects in the one or more test dies. In this manner, the method may include generating the standard reference die for a wafer and detecting defects on the wafer using output acquired for the same wafer. The standard reference die and the output for the one or more test dies may include images. In this manner, the standard reference die inspection may include image based inspection. The defects that are detected in the comparing step may include any of the defects described herein. For example, in one embodiment, the defects include repeater defects. In another embodiment, the defects include systematic defects caused by manufacturing of a reticle used to fabricate the wafer. In an additional embodiment, the defects include systematic defects, and the one or more test dies are formed on the wafer using a PWQ methodology. In some such embodiments, the one or more dies for which output is combined with the output of the centrally located die as described herein include one or more dies that are not adjacent to the centrally located die but are scattered across the wafer. The one or more test dies may be formed on the wafer using a PWQ methodology described in commonly owned U.S. Pat. No. 6,902,855 to Peterson et al., which is incorporated by reference as if fully set forth herein. The embodiments described herein may include any step(s) of any method(s) described in this patent.

In this manner, sources of systematic defects, which may be monitored as described herein, include defects caused by reticle manufacturing as well as systematic defects that are of interest in PWQ applications in which the systematic defects are used to determine the design process window or design process window marginality. In particular, the methods described herein can be advantageously used for product PWQ applications since the embodiments described herein can be used to provide suitable standard reference dies that may be otherwise lacking in such applications. In addition, the repeater defect detection approaches described herein may also be used to enhance traditional repeater defect detection applications such as repeater defect inspection of multi-die reticles. For example, in such applications, multiple test die may be used as described herein to obtain enhanced repeater defect signals and to reject random noise.

In one embodiment, all steps of the method are performed during run time of inspection of the wafer. In this manner, the method may include run time detection of repeater defects. For example, at the fundamental pixel comparison level, run time detection of repeater defects may include the above-described steps. In particular, a standard reference die image may be created during run time. The comparison may then be performed between two images, the standard reference die image and the test die image, to detect the repeater defects. Of course, more die may be inspected in the same fashion to obtain a wider set of statistics during run time. In such an implementation, the standard reference die may be stored (cached) in a computer system (e.g., on each leaf node of a parallel processor). In this manner, the embodiments described herein may utilize complementary inspection strategies to detect systematic defects by comparing output for a test die with output for an absolute reference.

In one embodiment, the method includes combining the output for two or more of the one or more test dies such that the combined output for the two or more test dies includes less noise from random defects than the output for each of the one or more test dies. For example, the "repeater" nature of the test die may be leveraged to amplify repeater S/N and to reject random noise (or random defects). In one such example, the test die may be created using output from multiple dies on the test wafer in a manner similar to that described above for creating the standard reference die. In addition, in one embodiment, the method includes combining the output for two or more of the one or more test dies, which may be performed as described herein, and the comparing step includes comparing the standard reference die to the combined output for the two or more test dies to detect the defects in the two or more test dies. In one such embodiment, the defects that are detected include repeater defects. In this manner, a relatively noise free standard reference die and a relatively noise free test die may be created, and reducing the noise in this manner will advantageously reduce detection of random defects.

One limitation of standard reference die based inspection may be the color or phase differences between the standard reference die wafer and the test die wafer. However, these issues may be successfully overcome by using BB DUV or BB EC mode in addition to one or more of many well tested global color compensation algorithms including auto-thresholding, MDAT, histogram equalization, etc. In particular, in one embodiment, the comparing step is performed using adaptive thresholding. For example, the basic comparison approach may use an adaptive thresholding algorithm such as MDAT, which can make the comparison relatively immune to color by thresholding using one or more statistics determined from multiple die.

In the methods described herein, truly local color variations that tend to repeat themselves within a wafer but are distinct across two wafers may cause a problem. However, such color variations tend to occur in more back end layers or due to errors in autofocus responses between the systems.

In some embodiments, the comparing step includes aligning the standard reference die and the output for the one or more test dies using equalization of histograms for the standard reference die and the one or more test dies. In this manner, a histogram equalization step may be used in the comparison step. Histogram equalization may generally include using histograms of one or more attributes such as gray level of output for two or more dies to determine if the histograms are different. If the histograms are sufficiently different, then the method may include performing a compensation on the output prior to the comparison to effectively normalize the images with respect to each other using the histograms thereby effectively mapping the images to each other using the histograms. As with all techniques, there is a point of diminishing returns with multiple approaches as interpolation noise sources may start dominating (and of course additional computing budgets).

In another embodiment, the comparing step includes template matching of a neighborhood of pixels in the standard reference die and a neighborhood of pixels in the output for the one or more test dies. In this manner, the method may include defect detection by template matching. For example, an alternative approach (which may be computationally more expensive) is to perform template matching in a 5 pixel by 5 pixel neighborhood. Either sum of squared differences (SSD) or normalized cross correlation (NCC) may be used for template matching. Any differences between the two images may be identified as a strong mismatch. Template matching may also be combined with the alignment step although the two steps usually differ because for alignment a larger search window may be used to ensure uniqueness and thereby relatively accurate alignment.

In one embodiment, acquiring the output of the inspection system for the wafer includes acquiring the output for only a portion of the test dies on the wafer. For example, statistically meaningful results for standard reference die based inspection can be acquired by inspecting only a fraction of the wafer (e.g., typically about five dies to about eight dies), which can be performed within one hour (lot hold sampling time). For example, unlike die-to-die inspection techniques used to detect random defects in which output generated for the whole wafer is used for random defect detection, the embodiments described herein can perform standard reference die inspection using output acquired for less than the whole wafer (e.g., output for only one die such as a centrally located die on the wafer). The additional time per pixel (which may be an order of magnitude less than traditional scan times) may be leveraged to acquire more photons per pass (e.g., for BB DUV EC mode for ADI layers or for multiple optical modes (multipass) to further increase S/N). In addition, the additional time per pixel may be leveraged to keep computing costs modest (e.g., about the same or slightly higher than current computing costs).

As described above, the output used to generate the standard reference die and the output for the test die(s) may be acquired for the same wafer. However, in other embodiments described further herein, the output used to generate the standard reference die may be acquired for a standard reference wafer while the output for the one or more test dies may be acquired for a different wafer.

In particular, an additional embodiment relates to a different method for inspecting a wafer. This method includes acquiring output of an inspection system for a standard reference wafer, which may be performed as described herein. The standard reference wafer may be fabricated in any suitable manner known in the art. The method also includes combining the output for a centrally located die on the standard reference wafer and one or more dies located on the standard reference wafer based on within die positions of the output. This combining step may be performed as described further herein. In addition, the method includes generating a standard reference die based on results of the combining step, which may be performed as described herein. For example, in one embodiment, the method includes aligning the standard reference die to design data space, and the generating step includes generating the standard reference die for only positions in the design data space corresponding to predetermined areas in the design data space. These steps may be performed as described herein. The standard reference die may be configured as described herein. For example, in one embodiment, the standard reference die includes substantially no noise from random defects in the centrally located die and the one or more dies.

The method further includes acquiring output of the inspection system for the wafer, which may be performed as described herein. For example, in one embodiment, acquiring the output of the inspection system for the wafer includes acquiring the output for only a portion of the test dies on the wafer, which may be performed as described further herein. In another embodiment, acquiring the output for the standard reference wafer and the wafer is performed using BB DUV mode inspection. In an additional embodiment, acquiring the output for the standard reference wafer and the wafer is performed using BB EC mode inspection.

Furthermore, the method includes comparing the standard reference die to output for one or more test dies on the wafer to detect defects in the one or more test dies, which may be performed as described herein. For example, in one embodiment, the comparing step is performed using adaptive thresholding, which may be performed as described above. In another example, in some embodiments, the comparing step includes aligning the standard reference die and the output for the one or more test dies using equalization of histograms for the standard reference die and the one or more test dies, which may be performed as described herein.

The output for the one or more test dies on the wafer that is compared to the standard reference die to detect the defects may be generated as described herein. For example, in one embodiment, the method includes combining the output for two or more of the one or more test dies such that the combined output for the two or more test dies includes less noise from random defects than the output for each of the one or more test dies. Such combining may be performed as described further herein. In another embodiment, the method includes combining the output for two or more of the one or more test dies, which may be performed as described herein, and the comparing step includes comparing the standard reference die to the combined output for the two or more test dies to detect the defects in the two or more test dies. In one such embodiment, the defects include repeater defects.

The defects that are detected in this method may include any of the defects described herein. For example, in one embodiment, the defects include repeater defects. In another embodiment, the defects include systematic defects caused by manufacturing of a reticle used to fabricate the wafer. In an additional embodiment, the defects include systematic defects, and the one or more test dies are formed on the wafer using a PWQ methodology.

The embodiments described herein may be configured to detect defects using a wafer-to-wafer comparison as described above because the embodiments may be configured to deal with system-to-system noise. For example, many errors on wafer inspection systems tend to be common moded since they are typically produced on the same system, generally close enough in wafer space to common mode out focus errors, data that is compared is taken inside the same optical field of view, etc. A lot of errors such as pixel size mismatch, time delay integration (TDI) camera rotation alignment errors, die-to-die alignment, etc. may therefore be effectively removed due to common mode or the RTA system. Some of these error sources include cumulative stitching error during setup, two-dimensional (2D) correlation error, optical distortion and magnification error, focus induced image translation, TDI rotation error, TDI rotation instability, TDI offset calibration error, TDI offset calibration instability (during setup or run), pixel rounding error, RTA runout, and RSS error.

In a die to standard reference die based inspection system, these errors become absolute errors and are therefore preferably approached systematically. In this manner, one of the major limitations to standard reference die based inspection may be wafer-to-wafer sub-pixel alignment. One approach to achieve less than about one pixel error wafer-to-wafer may be essentially to align the output for each wafer to design data space thereby effectively aligning the wafers to each other. For example, in one embodiment, the method includes determining a position of the standard reference die and a position of the output for the one or more test dies with respect to design data space prior to the comparing step and aligning the standard reference die and the output for the one or more test dies based on the positions of the standard reference die and the output for the one or more test dies with respect to the design data space prior to the comparing step. Aligning the output for wafers to design data space may be performed as described in commonly owned U.S. patent application Ser. No. 11/561,735 by Kulkarni et al., filed Nov. 20, 2006, published as U.S. Patent Application Publication No. 2007/0156379 on Jul. 5, 2007, which is incorporated by reference as if fully set forth herein. The embodiments described herein may include any step(s) of any method(s) described in this patent application.

Another approach that may be taken is to perform frame by frame alignment for comparison purposes. For example, in another embodiment, the method includes aligning the standard reference die to the output for the one or more test dies prior to the comparing step using a frame by frame alignment technique. Frame by frame alignment may include aligning every frame of the output acquired for the test die to a standard image. Aligning the frames to each other may include scaling, translating, etc., of the frames based on one or more attributes of the output. For example, aligning of the frames may be performed based on an average to average comparison, a statistical reference to statistical reference comparison, etc. Frame by frame alignment may include determining not only offset error between each pair of frames but also a scale factor error, which may be feasible since such alignment involves manipulation of the entire image. In addition, this alignment may be performed using a much larger overlap zone to account for runout errors (e.g., an overlap zone that is about twice as large as currently used overlap zones).

In addition to measurements made by alignment of the output for a wafer to design data space, the individual RTA errors may also be leveraged for standard reference die based inspection and inspection scan. For example, one advantage that RTA may have over an absolute reference system such as design data space is that RTA can be used to produce relative RTA offset curves. Therefore, global alignment may be managed with each swath, and the swaths may be aligned to each other using their respective RTA. For example, in one embodiment, the method includes aligning a first swath of the output for the one or more test dies with respect to a global alignment and aligning a second swath of the output for the one or more test dies to the first swath to thereby align the second swath to the global alignment.

Figure 4:
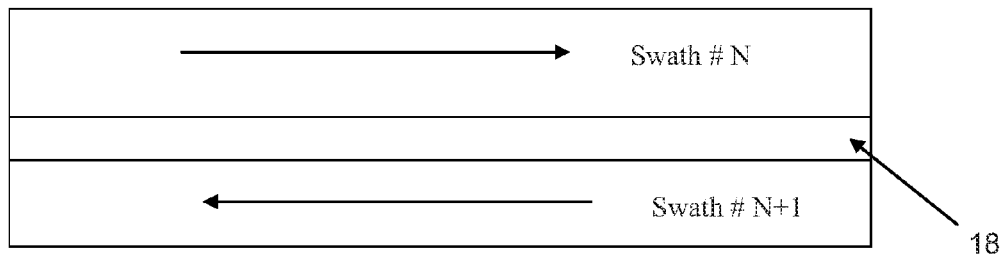
FIG. 4 is a schematic diagram illustrating a top view of one embodiment of consecutive swaths of output acquired for a wafer.
Figure 5:
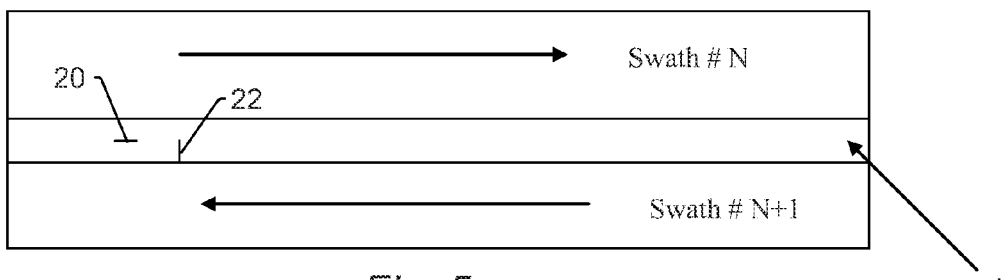
FIG. 5 is a schematic diagram illustrating a top view of one embodiment of consecutive swaths of output acquired for a wafer and a global alignment for determining the position of one swath with respect to another swath using output in a swath overlap region.

In one such embodiment, as shown in FIG. 4, two swaths N and N+1 of output may be acquired for a wafer (not shown in FIG. 4) by scanning the wafer in opposite directions as shown by the arrows within the swaths. As shown in FIG. 4, swaths N and N+1 partially overlap with each other in area 18 in wafer space. Therefore, both swaths will contain output for area 18. As such, the output for this area, which may include global alignment features, may be used to align one swath to another. In one such embodiment, FIG. 5 illustrates features 20 and 22 formed in inter-swath overlap area 18 in wafer space in which output for two successive scans overlap. Features 20 and 22 can be used for performing swath-to-swath registration. Features 20 and 22 may include any suitable global alignment features known in the art.

Whether such a system can achieve alignment errors of less than about 0.1 pixels, however, remains to be seen. Therefore, since an order of magnitude better accuracy than that which can be achieved by alignment to design data space is preferable for the embodiments described herein, active alignment between the test and standard reference dies may be performed.

For example, the methods described herein may use active RTA in which aliasing is also repeated to ensure that the degree to which the sampling is aliased allows an image to be properly constructed. In one embodiment, the output of the inspection system for the wafer includes at least two samples per illumination spot on the wafer. For example, for these techniques to work in the near term without the traditional BF RTA, a reticle inspection style wafer-to-wafer alignment technique (e.g., a wafer-to-wafer sub-pixel alignment technique) with optical modes that have sufficient sampling (e.g., greater than about 3.5 samples per PSF) may be used. For example, simulations suggest that for greater than about 3.5 spots per sample in the optics, minimal reconstruction error would be incurred. Furthermore, the methods may use certain deconvolution techniques to perform alignment. For example, if the inspection is performed with a substantially small pixel size that is substantially oversampled, the sensitivity of the inspection may be reduced. However, based on the PSF of the optics, the limits of the optics can be determined to determine appropriate parameters for the inspection.

From optical transform function (OTF) theory for incoherent illumination, the Raleigh distance is equal to about 0.61/NA, while for coherent illumination the resolution distance is equal to about 0.5/NA. Applying the Nyquist criteria of about 2 samples per spot at a minimum, the recommended reconstruction samples are determined to be at $R_c$ equal to about 0.3/NA for incoherent illumination and about 0.25/NA for coherent illumination, and for an NA of 0.9 an $R_c$ equal to about 2.92 samples for incoherent illumination and about 3.6 samples for coherent illumination. For undersampling errors (which can be expressed as a ratio of actual pixels to Nyquist pixels), aliasing errors will allow reconstruction of pixels acquired at ratios below 1.0. In addition, as the system, is moved into empty magnification space, the alignment interpolation errors will be reduced. One additional way to control the aliasing errors in EC mode is to stop down the NA independently.

The methods described herein may also include storing results of any of the steps described herein in a storage medium (such as that described further herein). For example, the method may include storing the generated standard reference die in the storage medium. The generated standard reference die may have any configuration described herein. In addition, the storing step may include storing results of the generating step in addition to any other results of any steps of any method embodiments described herein. The results may be stored in any manner known in the art. In addition, the storage medium may include any storage medium described herein or any other suitable storage medium known in the art. After the results have been stored, the results can be accessed in the storage medium and used by any of the method, system, or computer-readable medium embodiments as described herein, formatted for display to a user, used by another software module, method, or system, etc. Furthermore, the results may be stored "permanently," "semi-permanently," temporarily, or for some period of time. For example, the storage medium may be random access memory (RAM), and the results of the generating step may not necessarily persist indefinitely in the storage medium.

Another embodiment relates to a system configured to generate a standard reference die for use in a die to standard reference die inspection and/or to inspect a wafer. The system may be configured to generate the standard reference die according to any of the embodiments described herein. The system may also or alternatively be configured to inspect the wafer according to any of the embodiments described herein.

Figure 6:
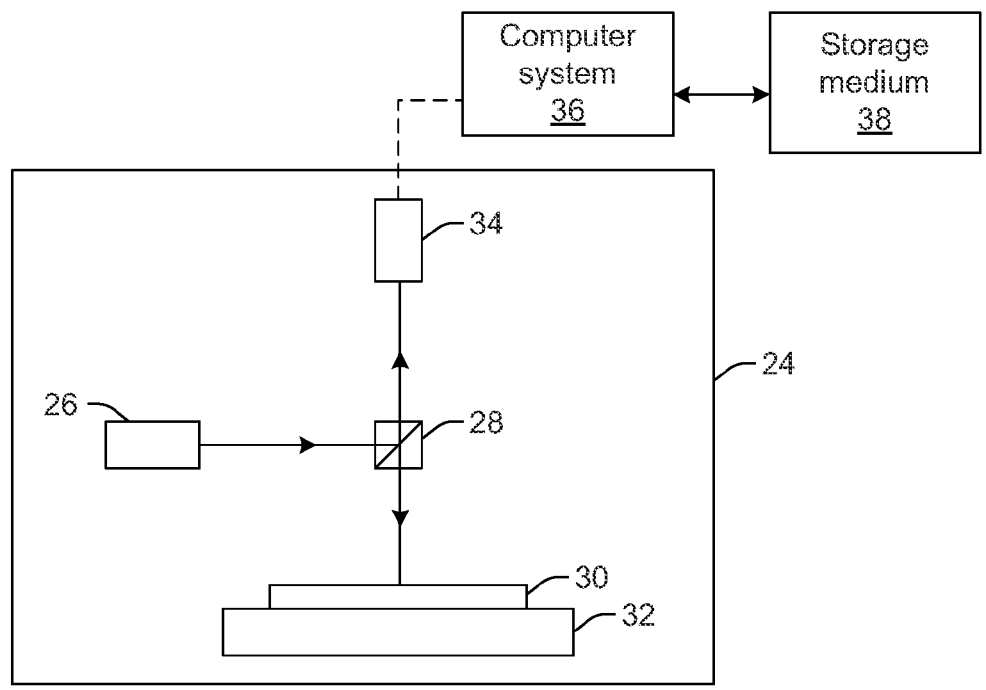
FIG. 6 is a schematic diagram illustrating a side view of one embodiment of a system configured to perform one or more embodiments described herein.

One embodiment of such a system is shown in FIG. 6. As shown in FIG. 6, in one embodiment, the system includes inspection system 24 configured to acquire output for wafers. Inspection system 24 includes light source 26 configured to direct light to beam splitter 28. The light source may include any suitable light source known in the art that is configured to generate light in any of the spectral region(s) (e.g., DUV) described herein. In addition, the light source may be configured to generate BB light and/or NB light such that the output can be acquired in a BB and/or NB spectral region. Beam splitter 28 may include any suitable optical component known in the art. Beam splitter 28 is configured to direct the light to wafer 30.

The inspection system may also include any other suitable optical component(s) (not shown) such as apertures positioned in the path of the light from light source 26 to wafer 30, which may be supported in the inspection system by stage 32.

Stage 32 may include any suitable robotic and/or mechanical assembly known in the art. Stage 32 may be configured to move the wafer (e.g., by rotation and/or translation) such that the light that is directed to the wafer can be scanned over the wafer in a scan path such as a serpentine scan path.

As further shown in FIG. 6, light from light source 26 may be directed to wafer 30 by beam splitter 28 at a substantially normal angle of incidence. However, the inspection system may be configured such that the light can be directed to the wafer at any suitable angle(s) of incidence. Light reflected from the wafer passes through beam splitter 28 to detector 34, which may include any suitable non-imaging detector or imaging detector known in the art. The inspection system may also include any other suitable optical component(s) (not shown) such as apertures positioned in the path of the light reflected from the wafer. Detector 34 is configured to generate output that is responsive to the light reflected from the wafer.

Although inspection system 24 is shown in FIG. 6 as a BF inspection system, the inspection system included in the system embodiments described herein may have any suitable configuration such as a DF configuration, an EC configuration, etc. In addition, the inspection system may be configured as an electron beam based inspection system. Furthermore, the inspection system may be configured such that one or more parameters of the inspection system are adjustable such that the inspection system can perform different modes of inspection. Moreover, the inspection system may be configured such that the inspection system can perform two or more modes of inspection simultaneously or sequentially.

Computer system 36 of the inspection system may be coupled to the detector in any suitable manner such that the computer system can receive the output generated by the detector. The computer system may be configured to perform one or more steps of one or more embodiments described herein using the output generated by detector 34 of inspection system 24. For example, the computer system may be configured to combine output acquired by inspection system 24 for a centrally located die on wafer 30 and one or more dies located on the wafer based on within die positions of the output. The computer system may also be configured to generate the standard reference die based on the combined output. In some embodiments, computer system 36 may be coupled to storage medium 38 such that the computer system may send results of one or more of the steps performed by the computer system to the storage medium.

The computer system may include any suitable computer system known in the art. For example, computer system 36 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Storage medium 38 may include any suitable storage medium known in the art such as a read-only memory, a random access memory, a magnetic or optical disk, or a magnetic tape.

The system described above may be further configured as described herein (e.g., to perform any other step(s) of any method(s) described herein).

Figure 7:
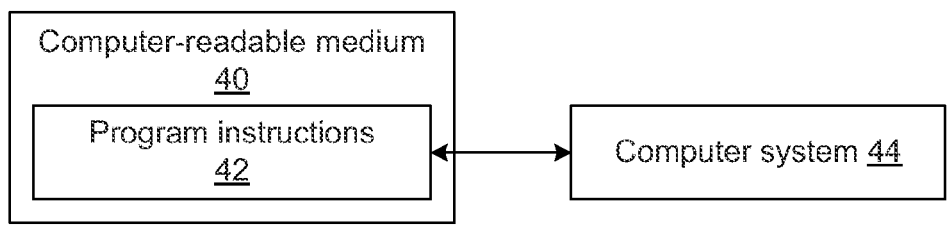
FIG. 7 is a block diagram illustrating one embodiment of a computer-readable medium that includes program instructions executable on a computer system for performing one or more embodiments described herein.

FIG. 7 illustrates one embodiment of computer-readable medium 40 that includes program instructions 42 executable on computer system 44 for performing a computer-implemented method for generating a standard reference die for use in a die to standard reference die inspection, a method for inspecting a wafer, a computer-implemented method for detecting defects on a wafer, or some combination thereof.

The method for which program instructions 42 are executable on computer system 44 may include any step(s) of any method(s) described herein. In some embodiments, computer system 44 may be a computer system of an inspection system such as computer system 36 shown in FIG. 4. However, in other embodiments, computer system 44 may not be coupled to or included in an inspection system. In some such embodiments, computer system 44 may be configured as a stand alone computer system. Computer-readable medium 40, program instructions 42, and computer system 44 may be further configured as described herein.

Program instructions 42 implementing methods such as those described herein may be transmitted over or stored on computer-readable medium 40. The computer-readable medium may be a transmission medium such as a wire, cable, or wireless transmission link. The computer-readable medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

A further embodiment relates to a computer-implemented method for detecting defects on a wafer. The method includes combining multiple images of a structure formed on the wafer to generate a composite image of the structure. The multiple images of the structure may be acquired as described further herein. The structure may include any structure formed on the wafer. Combining the multiple images of the structure may be performed as described further herein. In one embodiment, the combining step includes averaging the multiple images. Averaging the multiple images may be performed as described herein or in any other suitable manner using any suitable method and/or algorithm known in the art.

The multiple images are acquired at multiple positions on the wafer at which the structure is formed. In one embodiment, the multiple positions include positions of the structure in cells having identical designs. In another embodiment, the multiple positions include positions of the structure in neighboring dies. For example, during a PWQ type inspection, multiple dies from each focus and exposure point can be averaged together in a manner substantially similar to that performed by the MDAT algorithm. The multiple positions may be determined or identified as described herein or in any other suitable manner.

In one embodiment, the combining step is performed such that the composite image has less line edge roughness (LER) than each of the multiple images. In another embodiment, the combining step is performed such that the composite image has less random variation than each of the multiple images. For example, individual structures may have random variations such as LER that mask systematic errors. However, by averaging multiple images of the structure together, either from identical cells (e.g., adjacent identical cells) or from neighboring dies, a composite image can be constructed with much lower LER or random variation than any individual structure.

Figure 8:
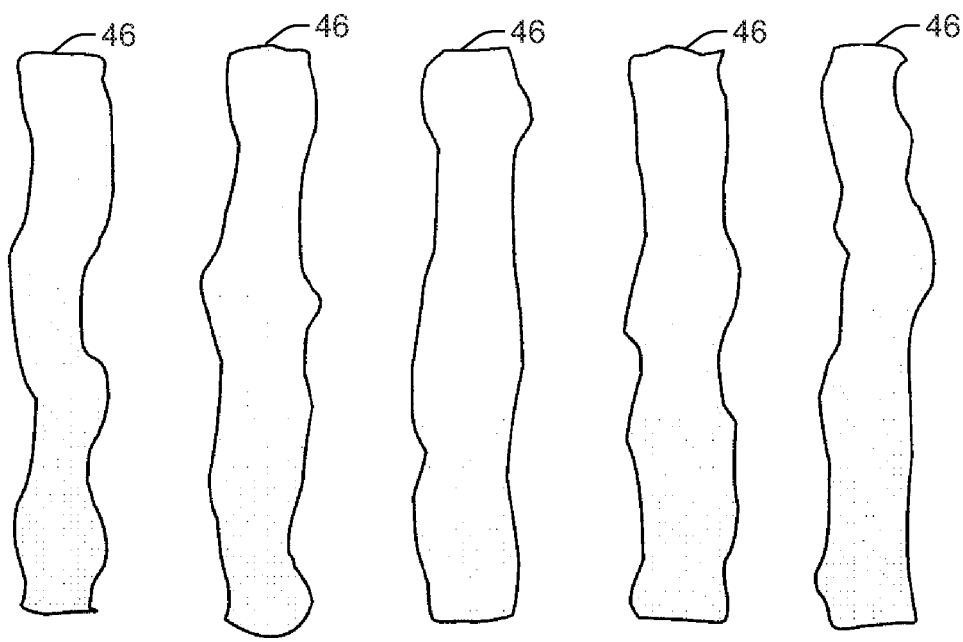
FIG. 8 is a schematic diagram illustrating various examples of multiple images of a structure formed on a wafer.
Figure 9:
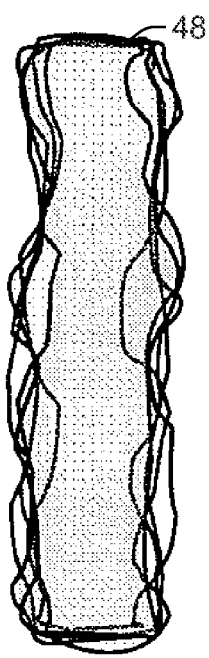
FIG. 9 is a schematic diagram illustrating one example of a composite image of the structure shown in the images of FIG. 8 generated by combining the multiple images of the structure shown in FIG. 8.

In one such example, as shown in FIG. 8, multiple images 46 of a structure formed on a wafer illustrate that the individual images of the individual features show LER. However, as shown in FIG. 9, composite image 48 of the structure generated by averaging the multiple images for the structure shown in FIG. 8 illustrates that the composite image of the structure has reduced LER compared to each of multiple images 46.

In a further embodiment, the combining step is performed such that the composite image has less gray level noise than each of the multiple images. For example, the composite image will contain less gray level noise from sources such as shot noise. In this manner, the embodiments described herein advantageously provide a reduction in shot noise and other image noise artifacts.

The method also includes comparing the composite image to a reference to detect defects on the wafer. In one embodiment, the reference includes a known good image of the structure. In another embodiment, the reference includes an image of the structure acquired in a standard reference die. In an additional embodiment, the reference includes a reference image, a composite test image, or a reference image and a composite test image of the structure acquired in a PWQ die. In some embodiments, the reference includes a rendered database image. In this manner, the composite image can be compared to either a known good image (from a standard reference die or a PWQ die) or to a rendered database image. In an additional embodiment, the reference includes a composite image of the structure generated from multiple images acquired at multiple positions on the wafer or on a different wafer. Such references may be generated as described further herein. In addition, the reference used in these embodiments may include any other references described herein.

In one embodiment, the defects include systematic defects. Systematic defects occur repeatedly within either an array structure of a single die or within the same structure on multiple die. Detecting such defects in the embodiments described herein may be advantageous since the embodiments described herein provide improved systematic defect detection. In particular, the embodiments described herein use multiple feature averaging to reduce random errors for improved systematic defect detection. In this manner, averaging multiple test images together improves inspection sensitivity for systematic defects. As such, the embodiments described herein provide improved sensitivity of systematic defects on a wafer inspection. In addition, the embodiments described herein advantageously provide reduced sensitivity to random nuisance defects. For example, as shown in FIG. 8, multiple images of the structure show LER that can be detected as false nuisance and therefore limit the sensitivity of the defect detection. However, the composite averaged image of the structure shown in FIG. 9 shows how the LER is reduced to allow better sensitivity to systematic line width (LW) variation.

In another embodiment, the defects have a size that is approximately equal to LER of the structure. For example, the embodiments described herein allow detection of systematic defects on a wafer (such as those occurring from incorrect optical proximity correction (OPC)) when the defect size is comparable to LER and other defects or variations. In contrast, some current inspection methods use a pixel-by-pixel comparison method between a test image and one or more reference images. However, if a random variation in either the test or reference image exists that is comparable to the systematic defect size, then the inspection will be overwhelmed by nuisance defects that will ultimately limit the inspection sensitivity. In this manner, systematic defects much smaller than possible in a conventional inspection can be detected in the embodiments described herein without an overwhelming nuisance defect detection rate. For example, the embodiments described herein may be used to extend the defect sensitivity of a conventional inspection system or a die-to-database inspection system to the sub-10 nm range.

Each of the embodiments of the computer-implemented method for detecting defects on a wafer described above may include any other step(s) of any other method(s) described herein. In addition, each of the embodiments of the computer-implemented method described above may be performed by any of the systems described herein.

Further modifications and alternative embodiments of various aspects of the invention may be apparent to those skilled in the art in view of this description. For example, methods for generating a standard reference die for use in a die to standard reference die inspection and methods for inspecting a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
    combining multiple images of a structure formed on the wafer to generate a composite image of the structure, wherein the multiple images are acquired at multiple positions on the wafer at which the structure is formed, wherein the multiple images comprise gray levels, wherein said combining comprises determining a mean value and a median value of the gray levels across within die positions, and wherein the composite image comprises the mean value across the within die positions;
    generating an additional composite image of the median value across the within die positions; and
    comparing the composite image to a reference to detect defects on the wafer.

2. The method of claim 1, wherein the defects comprise systematic defects.

3. The method of claim 1, wherein the defects have a size that is approximately equal to line edge roughness of the structure.

4. The method of claim 1, wherein said combining further comprises averaging the multiple images.

5. The method of claim 1, wherein the multiple positions comprise positions of the structure in cells having identical designs.

6. The method of claim 1, wherein the multiple positions comprise positions of the structure in neighboring dies.

7. The method of claim 1, wherein said combining is performed such that the composite image has less line edge roughness than each of the multiple images.

8. The method of claim 1, wherein said combining is performed such that the composite image has less random variation than each of the multiple images.

9. The method of claim 1, wherein said combining is performed such that the composite image has less gray level noise than each of the multiple images.

10. The method of claim 1, wherein the reference comprises a known good image of the structure.

11. The method of claim 1, wherein the reference comprises an image of the structure acquired in a standard reference die.

12. The method of claim 1, wherein the reference comprises a reference image, a composite test image, or a reference image and a composite test image of the structure acquired in a process window qualification die.

13. The method of claim 1, wherein the reference comprises a rendered database image.

14. The method of claim 1, wherein the reference comprises a composite image of the structure generated from multiple images acquired at multiple positions on the wafer or on a different wafer.

15. A system configured to detect defects on a wafer, comprising:
    an inspection system configured to acquire multiple images of a structure formed on the wafer; and
    a computer system configured for:
        combining the multiple images to generate a composite image of the structure, wherein the multiple images are acquired at multiple positions on the wafer at which the structure is formed, wherein the multiple images comprise gray levels, wherein said combining comprises determining a mean value and a median value of the gray levels across within die positions, and wherein the composite image comprises the mean value across the within die positions;
        generating an additional composite image of the median value across the within die positions; and
        comparing e composite image to a reference to detect defects on the wafer.

16. A non-transitory computer-readable medium comprising program instructions executable on a computer system for performing a computer-implemented method for detecting defects on a wafer, wherein the computer-implemented method comprises:
    combining multiple images of a structure formed on the wafer to generate a composite image of the structure, wherein the multiple images are acquired at multiple positions on the wafer at which the structure is formed, wherein the multiple images comprise gray levels, wherein said combining comprises determining a mean value and a median value of the gray levels across within die positions, and wherein the composite image comprises the mean value across the within die positions;
    generating an additional composite image of the median value across the within die positions; and
    comparing the composite image to a reference to detect defects on the wafer.

* * * * *